(12) United States Patent
Galka et al.

(10) Patent No.: US 10,093,651 B2
(45) Date of Patent: Oct. 9, 2018

(54) GHRELIN O-ACYL TRANSFERASE INHIBITORS

(71) Applicant: Eli Lilly and Company, Indianapolis, IN (US)

(72) Inventors: Christopher Stanley Galka, Carmel, IN (US); Erik James Hembre, Indianapolis, IN (US); Nicholas Allan Honigschmidt, Lakeville, MN (US); Maria Angeles Martinez-Grau, Madrid (ES); Gema Ruano Plaza, Madrid (ES); Almudena Rubio, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 27 days.

(21) Appl. No.: 15/561,159

(22) PCT Filed: Apr. 13, 2016

(86) PCT No.: PCT/US2016/027177
§ 371 (c)(1),
(2) Date: Sep. 25, 2017

(87) PCT Pub. No.: WO2016/168222
PCT Pub. Date: Oct. 20, 2016

(65) Prior Publication Data
US 2018/0086732 A1 Mar. 29, 2018

(30) Foreign Application Priority Data

Apr. 15, 2015 (EP) .................................. 15382180

(51) Int. Cl.
*C07D 401/06* (2006.01)
*C07D 401/14* (2006.01)

(52) U.S. Cl.
CPC ......... *C07D 401/06* (2013.01); *C07D 401/14* (2013.01)

(58) Field of Classification Search
None
See application file for complete search history.

(56) References Cited

U.S. PATENT DOCUMENTS 9,035,051 B1 * 5/2015 Martinez-Grau .... C07D 401/06
544/329
2005/0070712 A1 3/2005 Kosogof et al.

FOREIGN PATENT DOCUMENTS

WO 2013/125732 A1 8/2013

OTHER PUBLICATIONS

Khatib et al., Ghrelin O Acyl Transferase (GOAT) as a Novel Metabolic Regulatory Enzyme. Journal of Clinical and Diagnostic Research, 2015, 9, LE01-LE05.*

* cited by examiner

*Primary Examiner* — Po-Chih Chen
(74) *Attorney, Agent, or Firm* — Macharri Vorndran-Jones; Elizabeth Dingess Hammond

(57) ABSTRACT

The present invention provides novel GOAT inhibitors and their salts and pharmaceutical compositions thereof.

17 Claims, No Drawings

GHRELIN O-ACYL TRANSFERASE INHIBITORS

The present invention relates to compounds useful for inhibiting ghrelin O-acyl transferase (GOAT), pharmaceutical compositions and methods for treating diseases related to GOAT activity.

GOAT belongs to the membrane-bound O-acyl transferase (MBOAT) family of enzymes. It converts desacylghrelin (also known as unacylated ghrelin or UAG) to a biologically active form, acyl-ghrelin (AG), by transferring a fatty acid to the Ser3 residue of the desacylghrelin peptide. Acyl-ghrelin has been shown to increase food intake and increase adiposity in humans and in rodents. Infusion of AG in humans has also been shown to suppress glucose-induced insulin secretion. Elimination of the ghrelin gene has been shown to enhance insulin release to prevent or ameliorate glucose intolerance in high-fat diet fed ob/ob mice.

Small molecule GOAT inhibitors have been reported in the literature. See WO 2013/125732.

However, the prevalence of obesity and diabetes coupled with the variable effectiveness and responses to current treatments for obesity and diabetes necessitate that more treatment choices be available to patients. The present invention provides certain novel compounds that are GOAT inhibitors. Such new compounds could address the need for potent, effective treatment of obesity. It is further believed that a GOAT inhibitor may also be useful in reducing weight gain or weight regain as an adjunct to diet and/or exercise, other therapeutic medicinal agents or procedures designed to reducing weight gain or treat obesity. Similarly, a GOAT inhibitor may be useful in treating type 2 diabetes, singly or in combination with other treatments for type 2 diabetes.

The present invention provides a compound of formula

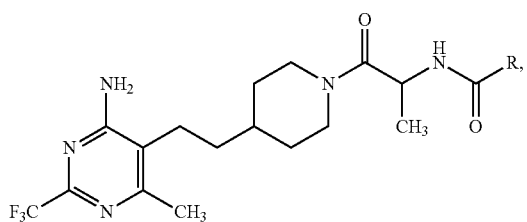

wherein R is selected from —$C_1$-$C_3$ alkyl optionally substituted with —OH; —O$C_1$-$C_4$ alkyl; pyrazolyl, oxazolyl, thiazolyl, or thiadiazolyl, wherein pyrazolyl, oxazolyl, or thiazolyl each may be optionally substituted one to two times with —$CH_3$; pyridinyl, pyridazinyl, or pyrazinyl, wherein each may be optionally substituted with —Cl; and phenyl optionally substituted with —O$CH_3$; or a pharmaceutically acceptable salt thereof.

The present invention provides a pharmaceutical composition comprising a compound of the invention, or a pharmaceutically acceptable salt thereof, with one or more pharmaceutically acceptable carriers, diluents, or excipients. In a further embodiment, the composition is used in combination with one or more other therapeutic agents.

A further aspect of the present invention provides a method of reducing weight gain or weight regain or treating type 2 diabetes or obesity comprising administering a compound of the present invention, or a pharmaceutically acceptable salt thereof, to a patient in need thereof.

The present invention also provides a compound of the invention, or a pharmaceutically acceptable salt thereof, for use in therapy, in particular for reducing weight gain or weight regain or treating type 2 diabetes or obesity. Even further, the present invention provides a compound of the invention, or a pharmaceutically acceptable salt thereof, for use in reducing weight gain or weight regain or treating type 2 diabetes or obesity. Furthermore, the present invention provides the use of a compound of the invention, or a pharmaceutically acceptable salt thereof, in the manufacture of a medicament for reducing weight gain or weight regain or treating type 2 diabetes or obesity.

The present invention further provides a method of treating the sequalae of an ischemic event comprising administering a compound of the present invention, or a pharmaceutically acceptable salt thereof, to a patient in need thereof. In a further embodiment, the ischemic event is myocardial ischemia or cardiac ischemia or cerebral ischemia.

In yet another aspect, the present invention provides a compound of the invention, or a pharmaceutically acceptable salt thereof, for use in therapy, in particular for treating the sequalae of an ischemic event. Even further, the present invention provides a compound of the invention, or a pharmaceutically acceptable salt thereof, for use in treating the sequalae of an ischemic event. Furthermore, the present invention provides the use of a compound of the invention, or a pharmaceutically acceptable salt thereof, in the manufacture of a medicament for treating the sequalae of an ischemic event. In a further embodiment, the ischemic event is myocardial ischemia or cardiac ischemia or cerebral ischemia.

The present invention further provides a method of treating addiction disorders comprising administering a compound of the present invention, or a pharmaceutically acceptable salt thereof, to a patient in need thereof. In a further embodiment, the addiction disorder involves consummatory behaviors, such as alcohol, smoking, overeating, or use of illicit drugs.

The present invention provides a method to ameliorate the consequences of stress that promote addictive behaviors comprising administering a compound of the present invention, or a pharmaceutically acceptable salt thereof, to a patient in need thereof. In a further embodiment, the addictive behaviors involve consummatory behaviors, such as alcohol, smoking, overeating, or use of illicit drugs.

The present invention also provides a compound of the invention, or a pharmaceutically acceptable salt thereof, for use in therapy, in particular for treating addiction disorders. Even further, the present invention provides a compound of the invention, or a pharmaceutically acceptable salt thereof, for use in treating addiction disorders. Furthermore, the present invention provides the use of a compound of the invention, or a pharmaceutically acceptable salt thereof, in the manufacture of a medicament for treating addiction disorders. In a further embodiment, the addiction disorder involves consummatory behaviors, such as alcohol, smoking, overeating, or use of illicit drugs.

The present invention also provides a compound of the invention, or a pharmaceutically acceptable salt thereof, for use in therapy, in particular for ameliorating the consequences of stress that promote addictive behaviors. In a further embodiment, the addiction disorder involves consummatory behaviors, such as alcohol, smoking, overeating, or use of illicit drugs. Even further, the present invention provides a compound of the invention, or a pharmaceutically acceptable salt thereof, for use in ameliorating the consequences of stress that promote addictive behaviors. Furthermore, the present invention provides the use of a compound of the invention, or a pharmaceutically acceptable salt thereof, in the manufacture of a medicament for ameliorating the consequences of stress that promote addictive behaviors. In a further embodiment, the addictive behaviors involve consummatory behaviors, such as alcohol, smoking, overeating, or use of illicit drugs.

The present invention also encompasses intermediates and processes useful for the synthesis of a compound of the present invention.

The term "treating" (or "treat" or "treatment") as used herein refers to restraining, slowing, stopping, or reversing the progression or severity of an existing symptom, condition or disorder.

As used herein, the term "reducing weight gain" refers to diminishing the increase in weight of a patient. The term "reducing weight regain" refers to diminishing the increase in weight of a patient experiencing rebound in weight after weight loss. Weight regain may be due to a rebound effect following cessation of weight loss achieved via diet, exercise, behavior modification, or approved therapies. For avoidance of doubt weight gain or weight regain as used herein refers to weight gain or weight regain induced by food intake or eating habits and does not refer to non-food related weight gain such as build up of fluids, weight due to water retention, muscle mass, or inflammation.

An "ischemic event" as used herein refers to an insufficient supply of blood to an organ or body part. The decrease in blood flow reduces the supply of oxygen to the affected organ or body part. An ischemic event may also be known as ischemia. One skilled in the art will know that ischemia can affect different organs or parts of the body, for example the heart, such as myocardial ischemia or cardiac ischemia, or the brain, such as cerebral ischemia.

"Addiction disorders" as used herein describes excessive maladaptive behaviors for which an individual exhibits an inability to control despite negative consequences. Of particular relevance to the present invention are addiction disorders involving consummatory behaviors such as alcohol intake, smoking, overeating, and use of illicit drugs. This invention normalizes aberrant incentive and reward neural substrates that are dysregulated in individuals with addictive disorders. Stress is often a precipitating agent in the etiology and maintenance of addictive disorders; this invention provides a method to ameliorate the consequences of stress that promote addictive behaviors.

A compound of the present invention may react to form pharmaceutically acceptable salts. Pharmaceutically acceptable salts and common methodology for preparing them are well known in the art. See, e.g., P. Stahl, et al. *Handbook of Pharmaceutical Salts: Properties, Selection and Use*, 2$^{nd}$ Revised Edition (Wiley-VCH, 2011); S. M. Berge, et al., "Pharmaceutical Salts," *Journal of Pharmaceutical Sciences*, Vol. 66, No. 1, January 1977.

The skilled artisan will appreciate that the compound of the invention, or pharmaceutically acceptable salt thereof, are comprised of a core that contains at least one chiral center, represented by * in (I) below:

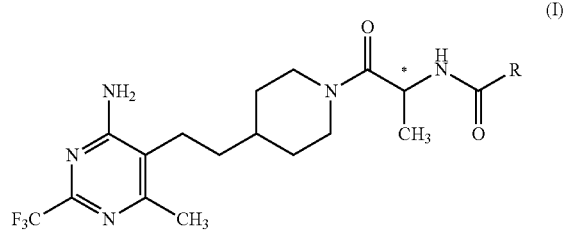

Preferred compounds of the invention are represented by (I):

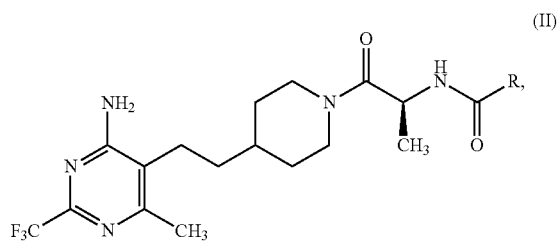

or pharmaceutically acceptable salts thereof.

The skilled artisan will appreciate that additional chiral centers may be created in the compounds of the invention by the selection of certain variables. The present invention contemplates all individual enantiomers or diastereomers, as well as mixtures of the enantiomers and diastereomers of said compounds including racemates.

The skilled artisan will also appreciate that the Cahn-Ingold-Prelog (R) or (S) designations for all chiral centers will vary depending upon the substitution patterns of the particular compound. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques at any convenient point in the synthesis of compounds of the invention. Single enantiomers of compounds of the invention are a preferred embodiment of the invention.

A compound of the present invention is preferably formulated as pharmaceutical compositions administered by a variety of routes, such as oral administration. Such pharmaceutical compositions and processes for preparing the same are well known in the art. See, e.g., *Remington: The Science and Practice of Pharmacy* (A. Gennaro, et al., eds., 21st ed., Mack Publishing Co., 2005). More particularly preferred, is a pharmaceutical composition comprising a compound of the invention represented by the formula

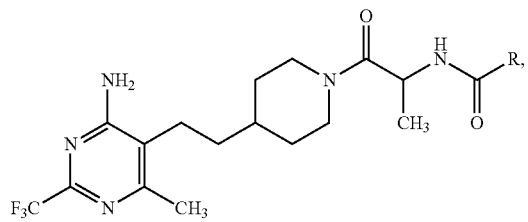

wherein R is selected from —C$_1$-C$_3$ alkyl optionally substituted with —OH; —OC$_1$-C$_4$ alkyl; pyrazolyl, oxazolyl, thiazolyl, or thiadiazolyl, wherein pyrazolyl, oxazolyl, or thiazolyl each may be optionally substituted one to two times with —CH$_3$; pyridinyl, pyridazinyl, or pyrazinyl, wherein each may be optionally substituted with —Cl; and phenyl optionally substituted with —OCH$_3$; or a pharmaceutically acceptable salt thereof and one or more pharmaceutically acceptable carriers or diluents.

Although all of the exemplified compounds of the invention are GOAT inhibitors, certain classes of compounds are preferred. The following paragraphs describe such preferred classes:

a) R is —C$_1$-C$_3$ alkyl optionally substituted with —OH; —OC$_1$-C$_4$ alkyl; pyrazolyl, oxazolyl, thiazolyl, or thiadiazolyl, wherein pyrazolyl, oxazolyl, or thiazolyl each may be optionally substituted one to two times with —CH$_3$; pyridinyl, pyridazinyl, or pyrazinyl, wherein each may be optionally substituted with —Cl; or phenyl optionally substituted with —OCH$_3$;
b) R is pyrazolyl, oxazolyl, thiazolyl, or thiadiazolyl, wherein pyrazolyl, oxazolyl, or thiazolyl each may be optionally substituted one to two times with —CH$_3$; pyridinyl or pyrazinyl, wherein each may be optionally substituted with —Cl; or phenyl optionally substituted with —OCH$_3$;
c) R is pyrazolyl, oxazolyl, thiazolyl, or thiadiazolyl, wherein pyrazolyl, oxazolyl, or thiazolyl each may be optionally substituted one to two times with —CH$_3$;
d) R is pyrazolyl, oxazolyl, thiazolyl, or thiadiazolyl, wherein pyrazolyl, oxazolyl, or thiazolyl each may be optionally substituted one to two times with —CH$_3$;
e) R is pyridinyl, pyridazinyl, or pyrazinyl, wherein each may be optionally substituted with —Cl;
f) R is phenyl optionally substituted with —OCH$_3$;
g) R is —CH$_3$ optionally substituted with —OH, —OCH$_3$, or —OC(CH$_3$)$_3$;
h) R is —CH$_3$ optionally substituted with —OH;
i) R is —OCH$_3$ or —OC(CH$_3$)$_3$;
j) R is pyrazolyl;
k) R is pyrazolyl substituted with —CH$_3$;
l) the compound of the present invention is the free base;
m) the methyl substituent adjacent to —NC(O)R is in the S configuration in the compound of the present invention;

A preferred embodiment of the present invention relates to compounds of the formula,

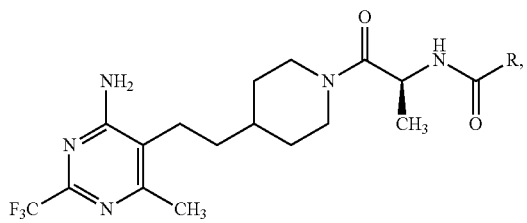

wherein R is selected from —C$_1$-C$_3$ alkyl optionally substituted with —OH; —OC$_1$-C$_4$ alkyl; pyrazolyl, oxazolyl, thiazolyl, or thiadiazolyl, wherein pyrazolyl, oxazolyl, or thiazolyl each may be optionally substituted one to two times with —CH$_3$; pyridinyl, pyridazinyl, or pyrazinyl, wherein each may be optionally substituted with —Cl; and phenyl optionally substituted with —OCH$_3$; or a pharmaceutically acceptable salt thereof.

Another preferred embodiment of the invention relates to compounds of the following formula

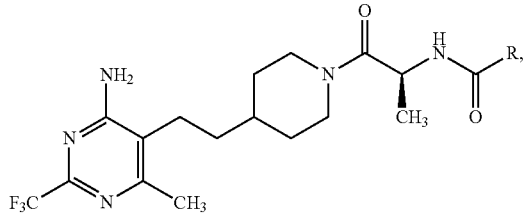

wherein R is selected from —CH$_3$ optionally substituted with —OH; —OCH$_3$ or —OC(CH$_3$)$_3$; pyrazolyl, oxazolyl, thiazolyl, or thiadiazolyl, wherein pyrazolyl, oxazolyl, or thiazolyl each may be optionally substituted one to two times with —CH$_3$; pyridinyl, pyridazinyl, or pyrazinyl, wherein each may be optionally substituted with —Cl; and phenyl optionally substituted with —OCH$_3$; or a pharmaceutically acceptable salt thereof.

Another preferred embodiment of the invention relates to compounds of the following formula

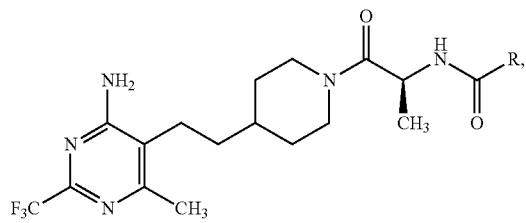

wherein R is selected from pyrazolyl, oxazolyl, thiazolyl, or thiadiazolyl, wherein pyrazolyl, oxazolyl, or thiazolyl each may be optionally substituted one to two times with —CH$_3$; pyridinyl, pyridazinyl, or pyrazinyl, wherein each may be optionally substituted with —Cl; and phenyl optionally substituted with —OCH$_3$; or a pharmaceutically acceptable salt thereof.

Another preferred embodiment of the invention relates to compounds of the following formula

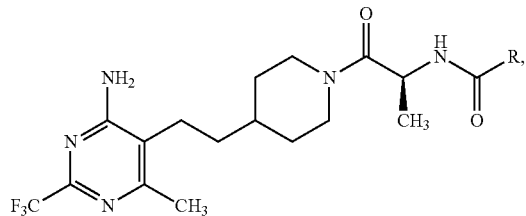

wherein R is selected from pyrazolyl, oxazolyl, thiazolyl, or thiadiazolyl, wherein pyrazolyl, oxazolyl, or thiazolyl each may be optionally substituted one to two times with —CH$_3$; pyridinyl or pyrazinyl, wherein each may be optionally substituted with —Cl; and phenyl optionally substituted with —OCH$_3$; or a pharmaceutically acceptable salt thereof.

Another preferred embodiment of the present invention relates to compounds of the formula,

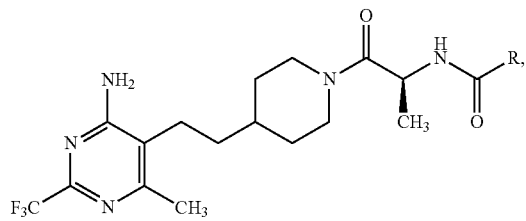

wherein R is selected from pyrazolyl, oxazolyl, thiazolyl, and thiadiazolyl, wherein pyrazolyl, oxazolyl, or thiazolyl each may be optionally substituted one to two times with —CH$_3$; or a pharmaceutically acceptable salt thereof.

A further preferred embodiment of the present invention relates to compounds of the formula:

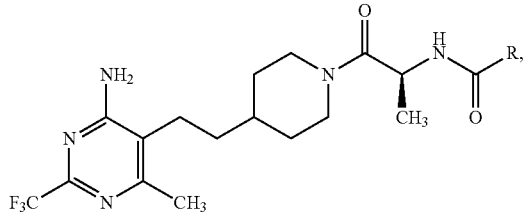

wherein R is selected from pyridinyl, pyridazinyl, and pyrazinyl, wherein each may be optionally substituted with —Cl; or a pharmaceutically acceptable salt thereof.

Another preferred embodiment of the invention relates to compounds of the following formula

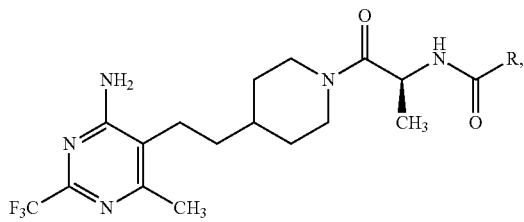

wherein R is phenyl optionally substituted with —OCH₃ or a pharmaceutically acceptable salt thereof.

Another preferred embodiment of the invention relates to compounds of the following formula

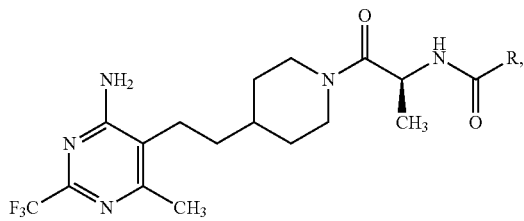

wherein R is selected from —CH₃ optionally substituted with —OH, —OCH₃, and —OC(CH₃)₃; or a pharmaceutically acceptable salt thereof.

Another preferred embodiment of the invention relates to compounds of the following formula

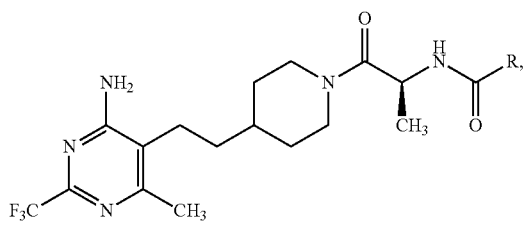

wherein R is —CH₃ optionally substituted with —OH; or a pharmaceutically acceptable salt thereof.

Another preferred embodiment of the invention relates to compounds of the following formula

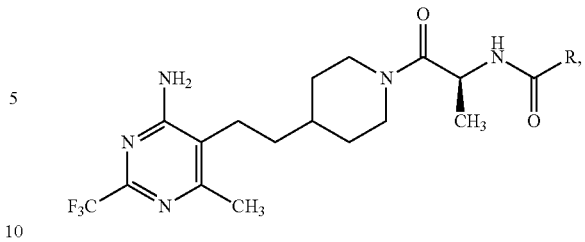

wherein R is selected from —OCH₃ and —OC(CH₃)₃; or a pharmaceutically acceptable salt thereof.

An especially preferred embodiment of the present invention relates to compounds of the formula:

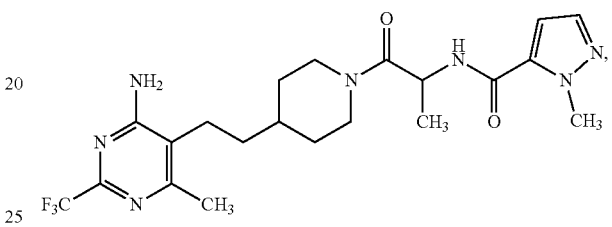

or a pharmaceutically acceptable salt thereof.

Another especially preferred embodiment of the present invention relates to the compound of the formula:

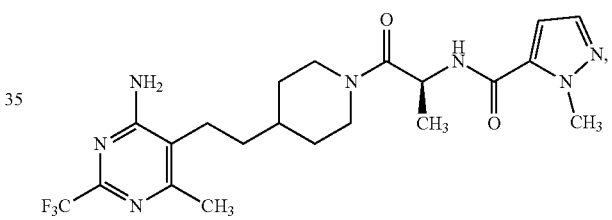

or a pharmaceutically acceptable salt thereof.

A further especially preferred embodiment of the present invention relates to the compound of formula:

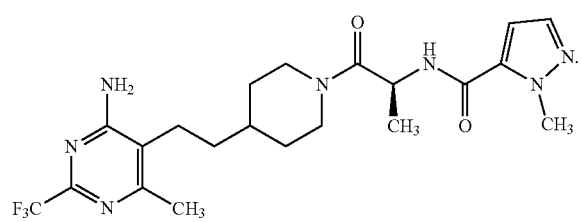 [SMILES: Cc1nc(C(F)(F)F)nc(N)c1CCC1CCN(C(=O)[C@H](C)NC(=O)c2ccnn2C)CC1]

The compound of the present invention is generally effective over a wide dosage range. For example, dosages per day fall within the range of about 0.03 to about 30 mg/Kg of body weight. In some instances dosage levels below the lower limit of the aforesaid range may be more than adequate, while in other cases still larger doses may be employed while maintaining a favorable benefit/risk profile, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

It is well known in the art that agents for the treatment of diabetes and/or obesity may be combined with other agents for the treatment of diabetes and/or obesity. The compound of the invention, or a pharmaceutically acceptable salt thereof, may be co-administered, simultaneously or sequentially, with other effective treatment(s) for diabetes or obesity. The compound of the invention, or a pharmaceutically acceptable salt thereof, alone or in combination with other effective treatment(s) may be administered, simultaneously or sequentially, following approved medical procedures such as bariatric surgeries, for example, gastric bypass surgery or adjustable gastric banding procedures.

The compounds of the present invention, or salts thereof, may be prepared by a variety of procedures known in the art, some of which are illustrated in the Schemes, Preparations, and Examples below. The specific synthetic steps for each of the routes described may be combined in different ways, or in conjunction with steps from different schemes, to prepare compounds or salts of the present invention. The products of each step in the Schemes below can be recovered by conventional methods well known in the art, including extraction, evaporation, precipitation, chromatography, filtration, trituration, and crystallization. In the Schemes below, all substituents unless otherwise indicated, are as previously defined. The reagents and starting materials are readily available to one of ordinary skill in the art.

Additionally, certain intermediates described in the following schemes may contain one or more nitrogen protecting groups. The variable protecting group may be the same or different in each occurrence depending on the particular reaction conditions and the particular transformations to be performed. The protection and deprotection conditions are well known to the skilled artisan and are described in the literature (See for example "Greene's Protective Groups in Organic Synthesis", Fourth Edition, by Peter G. M. Wuts and Theodora W. Greene, John Wiley and Sons, Inc. 2007).

Certain stereochemical centers have been left unspecified and certain substituents have been eliminated in the following schemes for the sake of clarity and are not intended to limit the teaching of the schemes in any way. Single enantiomers or diastereomers may be prepared beginning with chiral reagents or by stereoselective or stereospecific synthetic techniques. Alternatively, the single enantiomers or racemates may be isolated from mixtures by standard chiral chromatographic or crystallization techniques at any convenient point in the synthesis of compounds of the invention by methods such as selective crystallization techniques or chiral chromatography (See for example, J. Jacques, et al., "Enantiomers, Racemales, and Resolutions", John Wiley and Sons, Inc., 1981, and E. L. Eliel and S. H. Wilen, "Stereochemistry of Organic Compounds", Wiley-Interscience, 1994).

Some intermediates or compounds of the present invention may have one or more chiral centers. The present invention contemplates all individual enantiomers or diastereomers, as well as mixtures of the enantiomers and diastereomers of said compounds including racemates. It is preferred that compounds of the present invention containing at least one chiral center exist as a single enantiomer or diastereomer. The single enantiomer or diastereomer may be prepared beginning with chiral reagents or by stereoselective or stereospecific synthetic techniques. Alternatively, the single enantiomer or diastereomer may be isolated from mixtures by standard chiral chromatographic or crystallization techniques. The skilled artisan will appreciate that in some circumstances the elution order of enantiomers or diastereomers may be different due to different chromatographic columns and mobile phases.

Certain abbreviations are defined as follows: "ACN" refers to acetonitrile; "BSA" refers to Bovine Serum Albumin; "DCC" refers to 1,3-dicyclohexylcarbodiimide; "DCM" refers to dichloromethane; "DIC" refers to diisopropylcarbodiimide; "DIPEA" refers to diisopropylethylamine or N-ethyl-N-isopropyl-propan-2-amine; "DMAP" refers to dimethylaminopyridine; "DMF" refers to dimethylformamide; "DMSO" refers to dimethylsulfoxide; "EDCI" refers to 1-(3-dimethylaminopropyl)-3-ethylcarbodiimide hydrochloride; "EDTA" refers to ethylenediaminetetraacetic acid; "ee" refers to enantiomeric excess; "ELISA" refers to enzyme-linked immuno assay; "EtOAc" refers to ethyl acetate; "EtOH" refers to ethanol or ethyl alcohol; "Ex" refers to example; "FBS" refers to retal bovine serum; "HATU" refers to (dimethylamino)-N,N-dimethyl (3H-[1,2,3]triazolo[4,5-b]pyridin-3-yloxy)methaniminium hexafluorophosphate; "HOAt" refers to 1-hydroxy-7-azabenzotriazole; "HOBt" refers to 1-hydroxybenzotriazole hydrate; "HBTU" refers to refers to 2-(1H-benzotriazole-1-yl)-1,1,3,3-tetramethyluronium hexafluorophosphate; "HPLC" refers to High Performance Liquid Chromatography; "HRP" refers to horseradish peroxidase; "IC$_{50}$" refers to the concentration of an agent that produces 50% of the maximal inhibitory response possible for that agent; "LC-ES/MS" refers to Liquid Chromatography Electrospray Mass Spectrometry; "min" refers to minute or minutes; "MeOH" refers to methanol or methyl alcohol; "MS" refers to Mass Spectrometry; "OAc" refers to acetate; "PBS" refers to phosphate buffered saline, "PG" refers to protecting group; "Prep" refers to preparation; "PYBOP®" refers to benzotriazoi-1-yloxytripyrrolidino-phosphonium hexafluorophosphate; "PYBROP®" refers to bromo-tris-pyrrolidino phosphoniumhexafluoro phosphate; "RT" refers to room temperature; "SCX" refers to strong cation exchange; "SFC" refers to supercritical fluid chromatography; "SPE" refers to solid phase extraction; "TFA" refers to trifluoroacetic acid, "TMB" refers to 3,3',5,5'-tetramethylbenzidine; and "T$_R$" refers to time of retention.

In the Schemes below, all substituents unless otherwise indicated, are as previously defined. The reagents and starting materials are readily available to one of ordinary skill in the art. Others may be made by standard techniques of organic and heterocyclic chemistry which are analogous to the syntheses of known structurally-similar compounds and the procedures described in the Preparations and Examples which follow including any novel procedures.

Scheme 1

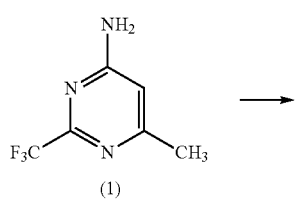

(1)

-continued

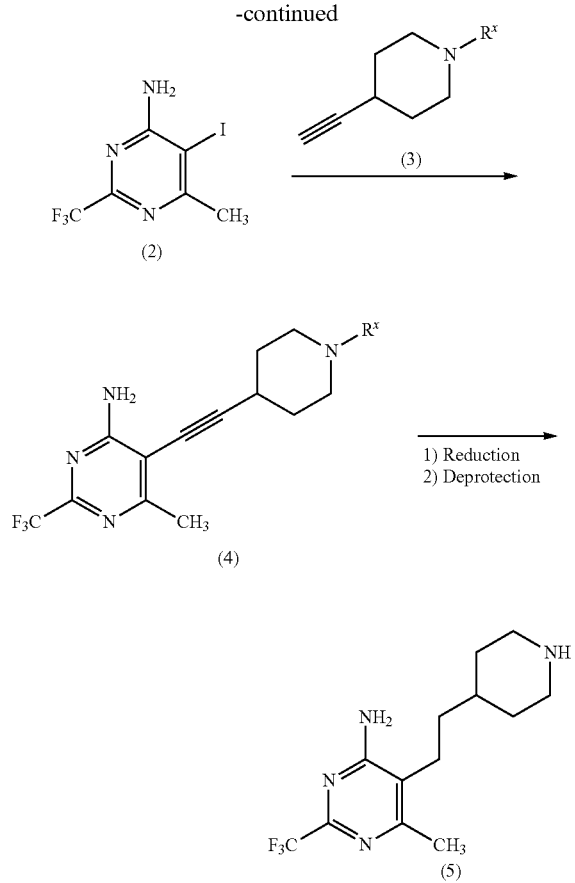

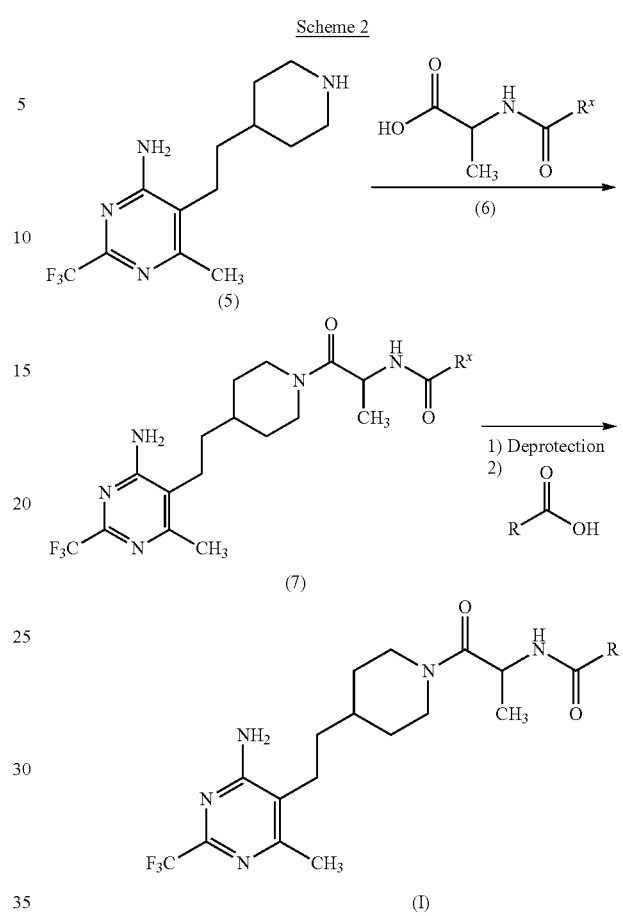

Scheme 2

In scheme 1, $R^x$ is an appropriate amine protecting group. Amine protecting groups are well known and appreciated in the art, and may include carbamates and amides. One skilled in the art will recognize alternative reagents and procedures to add and remove said protecting groups.

Compound (2) may be prepared by treating compound (1) with a halogenating agent, such as iodine monochloride, $I_2$, or N-iodosuccinimide. One skilled in the art will recognize that there are a number of methods of heteroaromatic halogenation. In a further step, compound (4) may be prepared by coupling compound (2) with an alkyne (3), under standard coupling conditions, utilizing a palladium derived organometallic reagent, such as $Pd(PPh_3)_2Cl_2$, $Pd(OAc)_2$, or $Pd_2(dba)_3$, in the presence of a catalyst, such as CuI, and a base, such as $Et_3N$, DIPEA, $K_2CO_3$, or $Cs_2CO_3$. One skilled in the art will recognize that there are alternative organometallic reagents derived from metals such as Cu or Zn. Alternatively, the corresponding free amine of compound (3) may be purchased and protected by an appropriate amine protecting group. Compound (4) is reduced by catalytic hydrogenation in the presence of a transition metal catalyst such as platinum oxide. Other hydrogenation catalysts are well known in the art; for example palladium on carbon or rhodium derivatives are known to reduce alkynes. One skilled in the art will recognize that there are other methods for alkyne reduction, including treatment with sodium in ethanol or zinc in acid. The protecting group can then be removed under conditions well known in the art, such as under acidic or basic conditions to provide compound (5).

Compound (7) may be synthesized by reacting compound (5) with compound (6), under standard coupling conditions. One skilled in the art will recognize that there are a number of methods and reagents for amide formation resulting from the reaction of carboxylic acids and amines. The coupling of compound (5) with compound (6) can be effected in the presence of a suitable coupling reagent and a suitable amine base, such as DIPEA or trimethylamine. Coupling reagents include carbodiimides, such as DCC, DIC, EDCI, and other coupling reagents, such as HOBt and HOAt. Additionally, uronium or phosphonium salts of non-nucleophilic anions, such as HATU, HBTU, PYBOP®, and PYBROP® can be used in place of the more traditional coupling reagents. Additives such as DMAP may be used to enhance the reactions. Alternatively, compound (5) can be acylated using substituted acyl chloride of compound (6) in the presence of a base, such as triethylamine or pyridine.

The protecting group, $R^x$, in intermediate (7) can be removed under conditions well known in the art, such as acidic or basic conditions. The resulting amine intermediate can be reacted with compound (8) under standard coupling conditions, including those previously described in the preparation of compound (7), to give a compound of Formula (I). The skilled artisan will recognize that there are alternative methods to prepare a compound of Formula (I) from deprotected compound (7), including reacting with an acid chloride in the presence of an organic base such as triethylamine or with an anhydride in the presence of a catalyst such as DMAP.

In an optional step, a pharmaceutically acceptable salt of a compound of Formula (I) can be formed by reaction of an appropriate free base of Formula (I) with an appropriate pharmaceutically acceptable acid in a suitable solvent under standard conditions. Additionally, the formation of such salts can occur simultaneously upon deprotection of a nitrogen protecting group. The formation of such salts is well known and appreciated in the art.

PREPARATIONS AND EXAMPLES

The following Preparations and Examples further illustrate the invention and represent typical synthesis of the compound of the invention. The reagents and starting materials are readily available or may be readily synthesized by one of ordinary skill in the art. It should be understood that the Preparations and Examples are set forth by way of illustration and not limitation, and that various modifications may be made by one of ordinary skill in the art.

The R or S configuration of the compound of the invention may be determined by standard techniques such as X-ray analysis and correlation with chiral-HPLC retention time. The naming of the following Preparations and Examples is generally performed using the IUPAC naming feature in MDL ACCELRYS® Draw version 4.1.

LC-ES/MS is performed on an AGILENT® HP1100 liquid chromatography system. Electrospray mass spectrometry measurements (acquired in positive mode) are performed on a Mass Selective Detector quadrupole mass spectrometer interfaced to the HP1100 HPLC. LC-MS conditions (low pH): column: PHENOMENEX® GEMINI® NX C18 2.1×50 mm 3.0 m; gradient: 5-100% B in 3 min, then 100% B for 0.75 min column temperature: 50° C.+/−10° C.; flow rate: 1 mL/min; Solvent A: deionized water with 0.1% formic acid; Solvent B: ACN with 0.1% formic acid. Alternate LC-MS conditions (low pH): column: XTERRA® MS C18 columns 2.1×50 mm, 3.5 um; gradient: 5% of solvent A for 0.25 min, gradient from 5% to 100% of solvent B in 3 min and 100% of solvent B for 0.5 min or 10% to 100% of solvent B in 3 min and at 100% of solvent B for 0.75 min; column temperature: 50° C.+/−10° C.; flow rate: 1 mL/min; Solvent A: 10 mM ammonium hydrogencarbonate pH 9; Solvent B: ACN; wavelength: 214 nm.

All preparative reversed phase chromatography is performed on an AGILENT® 1200 LC/M S equipped with a Mass Selective Detector mass spectrometer and a LEAP® autosampler/fraction collector. High pH methods are run on a 75×30 mm PHENOMENEX® GEMINI®-NX. 5µ particle size column with a 10×20 mm guard. Flow rate of 85 mL/min. Eluent is 10 mM ammonium bicarbonate (pH 10) in acetonitrile.

A Waters ZQ mass spectrometer and 29998 Diode Array Detector is used for acquiring mass and UV data during supercritical fluid chromatography (SFC). Material exhibiting the correct mass (electrospray ionization) and UV absorbance is collected.

Preparation 1

5-Iodo-6-methyl-2-(trifluoromethyl)pyrimidin-4-amine

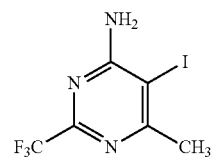

Add a solution of iodine monochloride (4.14 g, 23.37 mmol) in DCM (20.1 mL) to a flask containing 6-methyl-2-trifluoromethyl-pyrimidin-4-amine (4.14 g, 23.37 mmol) in MeOH (1.4 mL). Stir the mixture at room temperature for 48 hours. Upon reaction completion, add a 10% aqueous sodium sulfite solution (200 mL). Extract the resulting mixture with EtOAc (4×100 mL), dry the organic phase over $Na_2SO_4$, filter and concentrate under vacuum to obtain the crude title compound as a light yellow solid (7.0 g, 99%). Use material without additional purification. LC-ES/MS m/z 303.8 (M+H).

Preparation 2 tert-Butyl 4-[2-[4-amino-6-methyl-2-(trifluoromethyl)pyrimidin-5-yl]ethynyl]piperidine-1-carboxylate

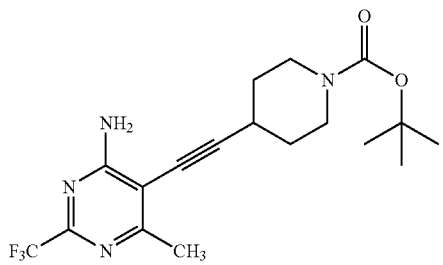 [SMILES: Cc1nc(C(F)(F)F)nc(N)c1C#CC1CCN(C(=O)OC(C)(C)C)CC1]

Slurry 5-iodo-6-methyl-2-(trifluoromethyl)pyrimidin-4-amine (2.05 g, 6.75 mmol), 4-ethynyl-piperidine-1-carboxylic acid tert-butyl ester (1.41 g, 6.75 mmol), bis(triphenylphosphine)palladium(II) chloride (239 mg, 0.34 mmol) and copper(I) iodide (1.30 mg, 0.68 mmol) in 10 mL DMF in a 20 mL microwave vial and bubble nitrogen through the suspension for 5 min. Add triethylamine (1.88 mL, 13.5 mmol) and continue to bubble nitrogen through the mixture for 5 additional min. Heat the mixture in a microwave at 100° C. for 60 min. Cool the mixture to room temperature and pour into saturated aqueous NaCl (500 mL). Extract with DCM, dry organic layer over $MgSO_4$, filter and concentrate under vacuum. Purify the resulting residue via chromatography over silica gel (5-35% EtOAc:hexanes over 45 min). Concentrate the purified fractions to dryness to obtain the title compound (1.25 g, 48%) as a light yellow solid. LC-ES/MS m/z 385.2 (M−H).

Preparation 3 tert-Butyl 4-[2-[4-amino-6-methyl-2-(trifluoromethyl)pyrimidin-5-yl]ethyl]piperidine-1-carboxylate

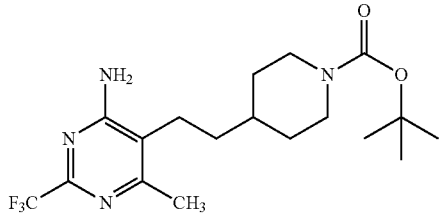 [SMILES: Cc1nc(C(F)(F)F)nc(N)c1CCC1CCN(C(=O)OC(C)(C)C)CC1]

Combine tert-butyl 4-[2-[4-amino-6-methyl-2-(trifluoromethyl)pyrimidin-5-yl]ethynyl]piperidine-1-carboxylate (6.28 g, 16.34 mmol) and platinum(IV) oxide (744 mg, 3.27 mmol) in EtOH (110 mL). Alternately evacuate and charge the flask with hydrogen under a hydrogen balloon, fill the system with hydrogen and agitate at room temperature for 18 hours. Filter the mixture through diatomaceous earth, rinsing with hot EtOH (30 mL) followed by 2M NH$_3$/MeOH (20 mL). Concentrate the solution under reduced pressure to obtain the title compound (6.15 g, 97%) as a white solid. Use without additional purification. LC-ES/MS m/z 389.2 (M+H).

Preparation 4

6-Methyl-5-[2-(4-piperidyl)ethyl]-2-(trifluoromethyl)pyrimidin-4-amine

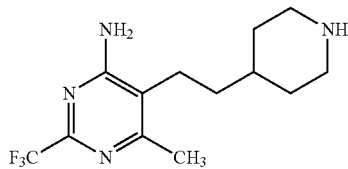

Dissolve tert-butyl 4-[2-[4-amino-6-methyl-2-(trifluoromethyl)pyrimidin-5-yl]ethyl]piperidine-1-carboxylate (6.07 g, 15.63 mmol) in DCM (25 mL) and add TFA (10 mL, 132.25 mmol). Stir the solution for 4 hours at room temperature. Concentrate the mixture under reduced pressure, dissolve resulting residue in DCM (15 mL) and apply to an SCX column (50 g), eluting with DCM (100 mL), MeOH (100 mL), and eluting desired material with 2M NH$_3$/MeOH (100 mL). Evaporate methanolic ammonia fractions to dryness to obtain the title compound (4.4 g, 97%) as an off-white solid. Use without additional purification. LC-ES/MS m/z 289.2 (M+H).

Preparation 5

6-Methyl-5-[2-(4-piperidyl)ethyl]-2-(trifluoromethyl)pyrimidin-4-amine dihydrochloride

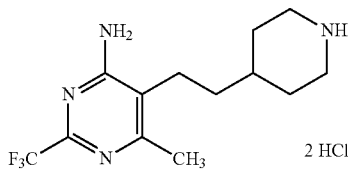 [SMILES: Cc1nc(C(F)(F)F)nc(N)c1CCC1CCNCC1]

Add acetyl chloride (180.1 mL) in a slow steady stream to a 50° C. solution of isopropanol (1.26 L) and stir at 50° C. for 30 min. Portionwise add tert-butyl 4-[2-[4-amino-6-methyl-2-(trifluoromethyl)pyrimidin-5-yl]ethyl]piperidine-1-carboxylate (180.1 g, 463.7 mmol) from preparation 3 and continue heating for 1.5 hours. Cool to RT and add diethyl ether (3.6 L). Collect solid by filtration and wash with diethyl ether (2×300 mL). Dry resulting solid in a vacuum oven at 50° C. overnight to obtain the title compound (174.0 g, 98%) as a white free-flowing powder. Use without additional purification. LC-ES/MS m/z 289.2 (M+H).

Example 1 tert-Butyl N-[(1S)-2-[4-[2-[4-amino-6-methyl-2-(trifluoromethyl)pyrimidin-5-yl]ethyl]-1-piperidyl]-1-methyl-2-oxo-ethyl]carbamate

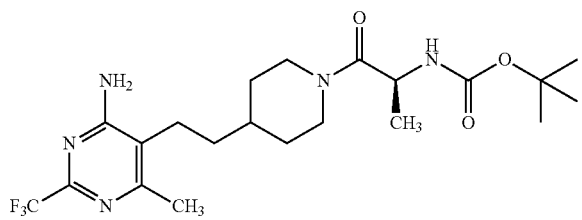 [SMILES: Cc1nc(C(F)(F)F)nc(N)c1CCC1CCN(C(=O)[C@H](C)NC(=O)OC(C)(C)C)CC1]

Dissolve 6-methyl-5-[2-(4-piperidyl)ethyl]-2-(trifluoromethyl)pyrimidin-4-amine (3.9 g, 13.53 mmol) in DMF (20 mL); add (2S)-2-(tert-butoxycarbonylamino)propanoic acid (2.8 g, 14.88 mmol), 1-hydroxybenzotriazole (7.46 g, 54.11 mmol), 1-(3-dimethylaminopropyl)-3-ethylcarbodiimide hydrochloride (2.63 g, 13.53 mmol) and diisopropylethylamine (7.08 mL, 40.58 mmol). Stir resulting mixture at room temperature overnight. Pour reaction mixture into saturated aqueous NaHCO$_3$ (500 mL) and extract with DCM. Dry organic phase over MgSO$_4$, filter, concentrate under vacuum and purify by chromatography over silica gel (10-75% EtOAc:hexanes over 45 min) to obtain, after solvent removal, the title compound (4.66 g, 75%) as a white foam. LC-ES/MS m/z 460.2 (M+H).

Alternative Procedure for Example 1 tert-Butyl N-[(1S)-2-[4-[2-[4-amino-6-methyl-2-(trifluoromethyl)pyrimidin-5-yl]ethyl]-1-piperidyl]-1-methyl-2-oxo-ethyl]carbamate

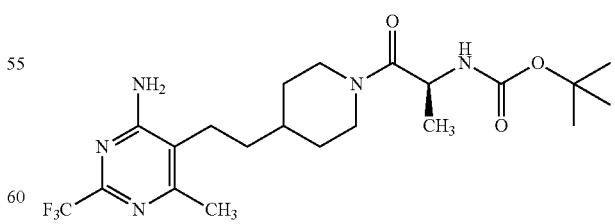

Add diisopropylethylamine (308.6 mL, 1770 mmol) to a suspension of 6-methyl-5-[2-(4-piperidyl)ethyl]-2-(trifluoromethyl)pyrimidin-4-amine dihydrochloride (170 g, 442.4 mmol), (2S)-2-(tert-butoxycarbonylamino)propanoic acid (92.1 g, 486.6 mmol) in DCM (1.6 L) to give a pale yellow suspension. Cool to 0° C. in an ice bath and portionwise add (dimethylamino)-N,N-dimethyl(3H-[1,2,3]triazolo[4,5-b]pyridin-3-yloxy)methaniminium hexafluorophosphate (167.3 g, 442.4 mmol). Stir bright yellow suspension at 0° C. for 30 min and warm to RT with stirring for 2 h. Concentrate to ca. 1 L under reduced pressure and dilute reaction mixture with EtOAc (1 L) and partition with saturated aqueous NH₄Cl (ca. 500 mL); separate organic layer and further extract aqueous layer with EtOAc (2×500 mL). Combine organic phases, wash with saturated aqueous NH₄Cl (4×400 mL), saturated aqueous NaHCO₃ (400 mL), water (400 mL), saturated aqueous NaCl (400 mL). Dry over MgSO₄, filter and concentrate under reduced pressure, azeotroping with iso-hexanes (750 ml) to obtain the title compound (237 g, 99%) as a white foam, suitable for use without additional purification. LC-ES/MS m/z 460.3 (M+H). Chiral analysis (SFC MiniGram®, 15% MeOH/CO2/0.2% isopropylamine, 5 mL/min, 100 bar, 35° C., 220 nm)>98% ee.

Preparation 6

(2S)-2-Amino-1-[4-[2-[4-amino-6-methyl-2-(trifluoromethyl)pyrimidin-5-yl]ethyl]-1-piperidyl]propan-1-one

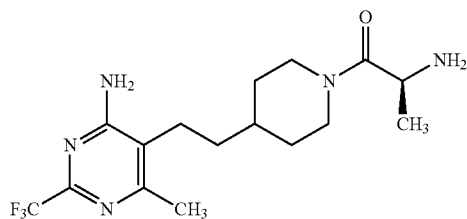 [SMILES: Cc1nc(C(F)(F)F)nc(N)c1CCC1CCN(C(=O)[C@H](C)N)CC1]

Dissolve tert-butyl N-[(LS)-2-[4-[2-[4-amino-6-methyl-2-(trifluoromethyl)pyrimidin-5-yl]ethyl]-1-piperidyl]-1-methyl-2-oxo-ethyl]carbamate (4.66 g, 10.14 mmol) in DCM (150 nL) and add trifluoroacetic acid (7.67 mL, 101.4 mmol). Stir resulting mixture at room temperature overnight. Concentrate solvent under vacuum, reconstitute residue in DCM (20 mL) and apply to an SCX column (50 g), eluting with 100 nL DCM, 100 mL MeOH, and elating desired material with 2M NH₃/MeOH (100 ml). Evaporate methanolic ammonia fractions to dryness to obtain the title compound (3.58 g, 98%) as a white foam. Use without additional purification. LC-ES/MS m/z 360.2 (M+H).

Example 2

N-[(1 S)-2-[4-[2-[4-Amino-6-methyl-2-(trifluoromethyl)pyrimidin-5-yl]ethyl]-1-piperidyl]-1-methyl-2-oxo-ethyl]-2-methyl-pyrazole-3-carboxamide

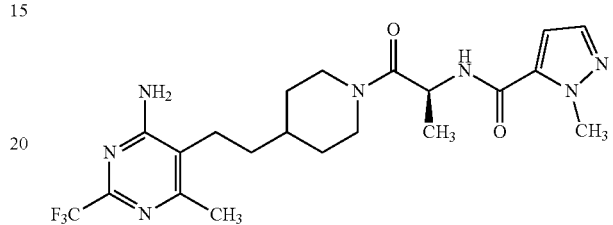

Dissolve (2S)-2-amino-1-[4-[2-[4-amino-6-methyl-2-(trifluoromethyl)pyrimidin-5-yl]ethyl]-1-piperidyl]propan-1-one (560 mg, 1.56 mmol) in DCM (20 mL) containing DMF (3 mL); add 1-methyl-1H-pyrazole-5-carboxylic acid (216 mg, 1.71 mmol), 1-hydroxybenzotriazole (969 mg, 6.23 mmol), 1-(3-dimethylaminopropyl)-3-ethylcarbodiimide hydrochloride (303 mg, 1.56 mmol) and diisopropylethylamine (1.36 mL, 7.8 mmol). Stir resulting mixture at room temperature overnight. Pour reaction mixture into saturated aqueous NaHCO₃ (200 mL) and extract with DCM. Dry organic phase over MgSO₄, filter, concentrate under vacuum and purify by chromatography over silica gel (0-10% MeOH:DCM over 30 min) to obtain, after solvent removal, the title compound (665 mg, 91%) as a white foam. LC-ES/MS m/z 468.0 (M+H).

Prepare the Examples in Table 1 below by essentially following the procedure described in Example 2, using (2S)-2-amino-1-[4-[2-[4-amino-6-methyl-2-(trifluoromethyl)pyrimidin-5-yl]ethyl]-1-piperidyl]propan-1-one and the appropriately substituted carboxylic acid.

TABLE 1

| Ex. No. | Structure | Name | Yield | ES/MS m/z (M + H) |
|---|---|---|---|---|
| 3 | 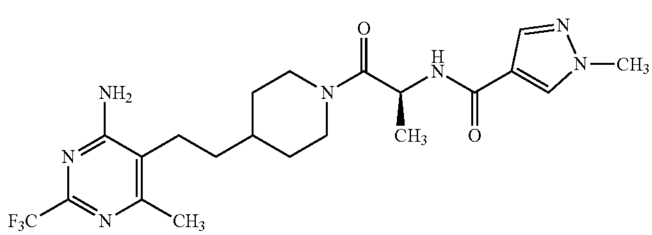 [SMILES: Cc1nc(C(F)(F)F)nc(N)c1CCC1CCN(C(=O)[C@H](C)NC(=O)c2cnn(C)c2)CC1] | N-[(1S)-2-[4-[2-[4-Amino-6-methyl-2-(trifluoromethyl)pyrimidin-5-yl]ethyl]-1-piperidyl]-1-methyl-2-oxo-ethyl]-1-methyl-pyrazole-4-carboxamide | 58% | 468.3 |

TABLE 1-continued

| Ex. No. | Structure | Name | Yield | ES/MS m/z (M + H) |
|---|---|---|---|---|
| 4 | 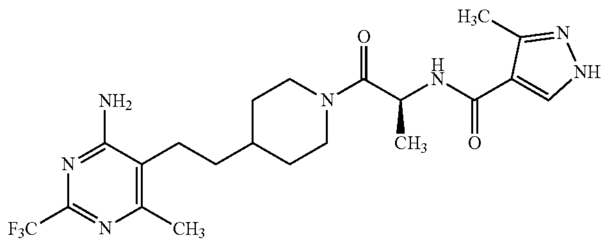 [SMILES: Cc1n[nH]cc1C(=O)N[C@@H](C)C(=O)N1CCC(CCc2c(C)nc(C(F)(F)F)nc2N)CC1] | N-[(1S)-2-[4-[2-[4-Amino-6-methyl-2-(trifluoromethyl)pyrimidin-5-yl]ethyl]-1-piperidyl]-1-methyl-2-oxo-ethyl]-3-methyl-1H-pyrazole-4-carboxamide | 43% | 468.3 |
| 5 | 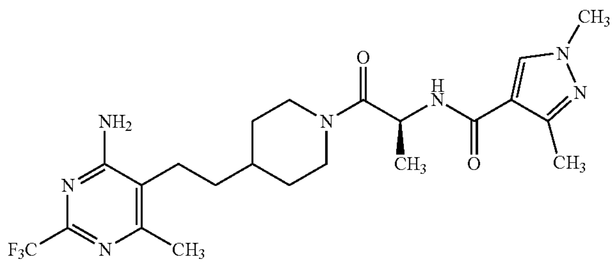 [SMILES: Cc1nn(C)cc1C(=O)N[C@@H](C)C(=O)N1CCC(CCc2c(C)nc(C(F)(F)F)nc2N)CC1] | N-[(1S)-2-[4-[2-[4-Amino-6-methyl-2-(trifluoromethyl)pyrimidin-5-yl]ethyl]-1-piperidyl]-1-methyl-2-oxo-ethyl]-1,3-dimethyl-pyrazole-4-carboxamide | 61% | 482.3 |
| 6 | 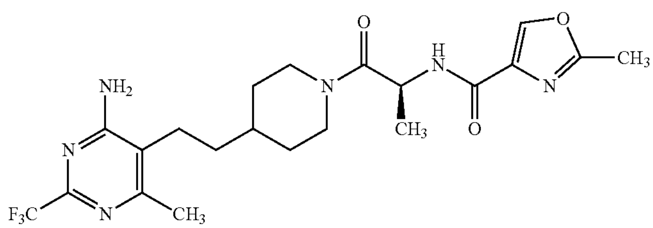 [SMILES: Cc1nc(C(=O)N[C@@H](C)C(=O)N2CCC(CCc3c(C)nc(C(F)(F)F)nc3N)CC2)co1] | N-[(1S)-2-[4-[2-[4-Amino-6-methyl-2-(trifluoromethyl)pyrimidin-5-yl]ethyl]-1-piperidyl]-1-methyl-2-oxo-ethyl]-2-methyl-oxazole-4-carboxamide | 10% | 468.6 |
| 7 | 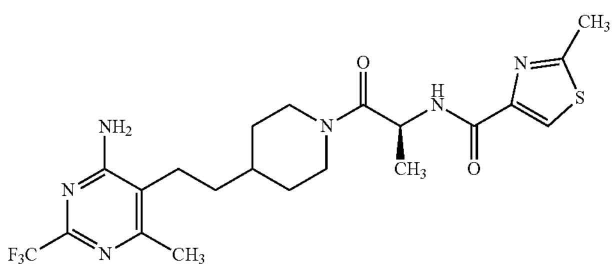 [SMILES: Cc1nc(C(=O)N[C@@H](C)C(=O)N2CCC(CCc3c(C)nc(C(F)(F)F)nc3N)CC2)cs1] | N-[(1S)-2-[4-[2-[4-Amino-6-methyl-2-(trifluoromethyl)pyrimidin-5-yl]ethyl]-1-piperidyl]-1-methyl-2-oxo-ethyl]-2-methyl-thiazole-4-carboxamide | 59% | 484.6 |
| 8 | 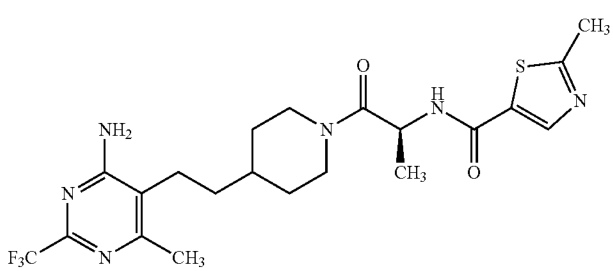 | N-[(1S)-2-[4-[2-[4-Amino-6-methyl-2-(trifluoromethyl)pyrimidin-5-yl]ethyl]-1-piperidyl]-1-methyl-2-oxo-ethyl]-2-methyl-thiazole-5-carboxamide | 58% | 485.0 |
| 9 | 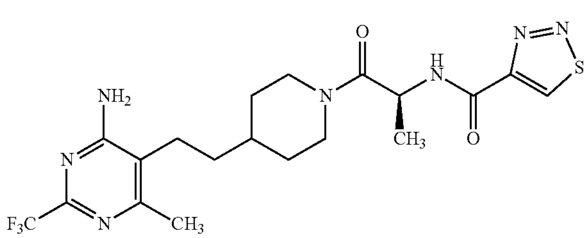 [SMILES: Cc1nc(C(F)(F)F)nc(N)c1CCC1CCN(C(=O)[C@H](C)NC(=O)c2csnn2)CC1] | N-[(1S)-2-[4-[2-[4-Amino-6-methyl-2-(trifluoromethyl)pyrimidin-5-yl]ethyl]-1-piperidyl]-1-methyl-2-oxo-ethyl]thiadiazole-4-carboxamide | 64% | 471.6 |

TABLE 1-continued

| Ex. No. | Structure | Name | Yield | ES/MS m/z (M + H) |
|---|---|---|---|---|
| 10 | 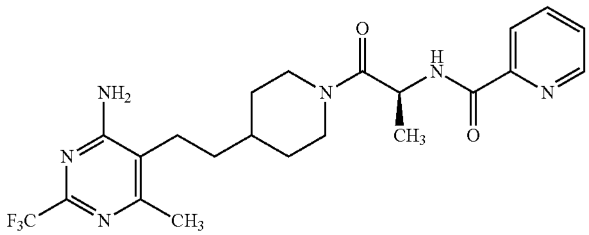 [SMILES: Cc1nc(C(F)(F)F)nc(N)c1CCC1CCN(C(=O)[C@H](C)NC(=O)c2ccccn2)CC1] | N-[(1S)-2-[4-[2-[4-Amino-6-methyl-2-(trifluoromethyl)pyrimidin-5-yl]ethyl]-1-piperidyl]-1-methyl-2-oxo-ethyl]pyridine-2-carboxamide | 89% | 465.2 |
| 11 | 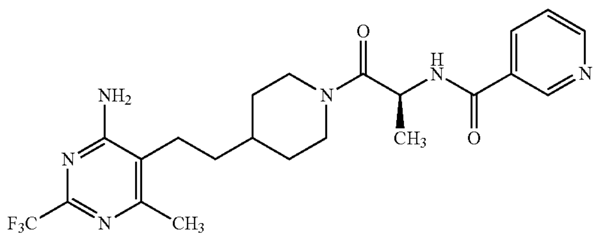 [SMILES: Cc1nc(C(F)(F)F)nc(N)c1CCC1CCN(C(=O)[C@H](C)NC(=O)c2cccnc2)CC1] | N-[(1S)-2-[4-[2-[4-Amino-6-methyl-2-(trifluoromethyl)pyrimidin-5-yl]ethyl]-1-piperidyl]-1-methyl-2-oxo-ethyl]pyridine-3-carboxamide | 62% | 465.3 |
| 12 | 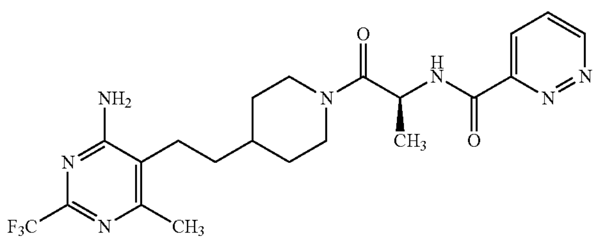 [SMILES: Cc1nc(C(F)(F)F)nc(N)c1CCC1CCN(C(=O)[C@H](C)NC(=O)c2cccnn2)CC1] | N-[(1S)-2-[4-[2-[4-Amino-6-methyl-2-trifluoromethyl)pyrimidin-5-yl]ethyl]-1-piperidyl]-1-methyl-2-oxo-ethyl]pyridazine-3-carboxamide | 11% | 466.0 |
| 13 | 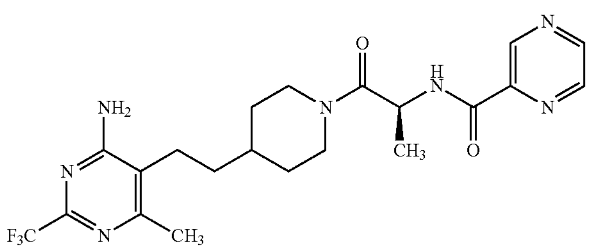 | N-[(1S)-2-[4-[2-[4-Amino-6-methyl-2-(trifluoromethyl)pyrimidin-5-yl]ethyl]-1-piperidyl]-1-methyl-2-oxo-ethyl]pyrazine-2-carboxamide | 67% | 466.2 |
| 14 | 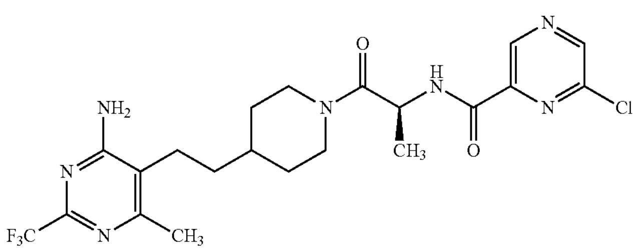 [SMILES: Cc1nc(C(F)(F)F)nc(N)c1CCC1CCN(C(=O)[C@H](C)NC(=O)c2cncc(Cl)n2)CC1] | N-[(1S)-2-[4-[2-[4-Amino-6-methyl-2-(trifluoromethyl)pyrimidin-5-yl]ethyl]-1-piperidyl]-1-methyl-2-oxo-ethyl]-6-chloro-pyrazine-2-carboxamide | 12% | 500.3/502.3 ($^{35}$Cl/$^{37}$Cl) |
| 15 | 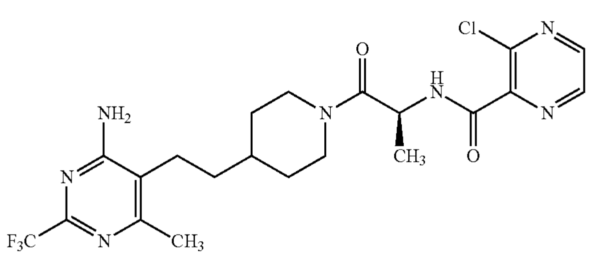 [SMILES: Cc1nc(C(F)(F)F)nc(N)c1CCC1CCN(C(=O)[C@H](C)NC(=O)c2nccnc2Cl)CC1] | N-[(1S)-2-[4-[2-[4-Amino-6-methyl-2-(trifluoromethyl)pyrimidin-5-yl]ethyl]-1-piperidyl]-1-methyl-2-oxo-ethyl]-3-chloro-pyrazine-2-carboxamide | 49% | 500.3/502.3 ($^{35}$Cl/$^{37}$Cl) |

TABLE 1-continued

| Ex. No. | Structure | Name | Yield | ES/MS m/z (M + H) |
|---|---|---|---|---|
| 16 | 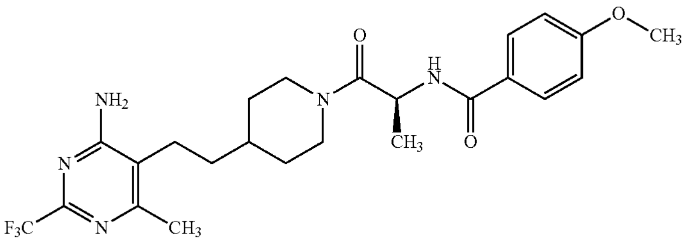 [SMILES: COc1ccc(C(=O)N[C@@H](C)C(=O)N2CCC(CCc3c(C)nc(C(F)(F)F)nc3N)CC2)cc1] | N-[(1S)-2-[4-[2-[4-Amino-6-methyl-2-(trifluoromethyl)pyrimidin-5-yl]ethyl]-1-piperidyl]-1-methyl-2-oxo-ethyl]-4-methoxy-benzamide | 62% | 494.2 |
| 17 | 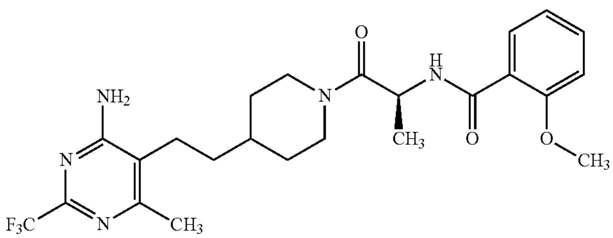 [SMILES: COc1ccccc1C(=O)N[C@@H](C)C(=O)N1CCC(CCc2c(C)nc(C(F)(F)F)nc2N)CC1] | N-[(1S)-2-[4-[2-[4-Amino-6-methyl-2-(trifluoromethyl)pyrimidin-5-yl]ethyl]-1-piperidyl]-1-methyl-2-oxo-ethyl]-2-methoxy-benzamide | 74% | 494.3 |
| 18 | 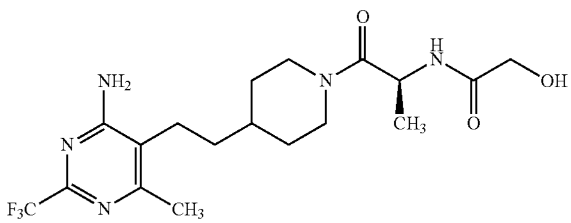 [SMILES: Cc1nc(C(F)(F)F)nc(N)c1CCC1CCN(C(=O)[C@H](C)NC(=O)CO)CC1] | N-[(1S)-2-[4-[2-[4-Amino-6-methyl-2-(trifluoromethyl)pyrimidin-5-yl]ethyl]-1-piperidyl]-1-methyl-2-oxo-ethyl]-2-hydroxy-acetamide | 99% | 418.2 |

Alternative Method of Preparation for Example 2

N-[(1S)-2-[4-[2-[4-Amino-6-methyl-2-(trifluoromethyl)pyrimidin-5-yl]ethyl]-1-piperidyl]-1-methyl-2-oxo-ethyl]-2-methyl-pyrazole-3-carboxamide

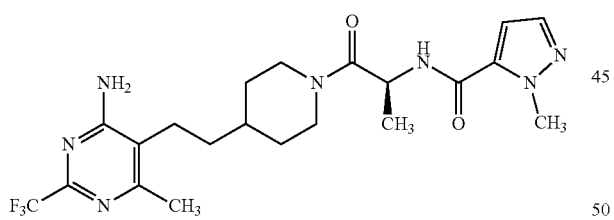

Add a slow, steady stream of 1-propanephosphonic acid cyclic anhydride (410.6 mL, 683.9 mmol) to a slurry of (2S)-2-amino-1-[4-[2-[4-amino-6-methyl-2-(trifluoromethyl)pyrimidin-5-yl]ethyl]-1-piperidyl]propan-1-one (168.0 g, 342.0 mmol), 1-methyl-1H-pyrazole-5-carboxylic acid (64.7 g, 513.0 mmol) and diisopropylethylamine (244.5 mL, 1400 mmol) suspended in DCM (1.5 L) in an ice bath, maintaining the internal temperature at 5-10° C. Warm to RT with stirring over 2.5 hours. Concentrate to ca. 500 mL under reduced pressure and dilute resulting residue with EtOAc (2 L) and water (1 L), separate layers, extract aqueous layer with EtOAc (2×400 mL) and wash combined organic layers with saturated $NH_4Cl$ (500 mL), saturated aqueous $NaHCO_3$ (1 L), water (500 mL), saturated aqueous NaCl (500 mL). Dry organic layer over $MgSO_4$, filter, evaporate under reduced pressure. Dissolve resulting residue in isopropyl acetate (180 mL), treat with heptanes (1 L) and heat to 70° C. for 4 hours to eject a white powder. Cool to RT, collect solids by filtration, wash with 9:1 heptane: isopropyl acetate (100 mL) followed by heptanes (2×100 mL). Dry in vacuum oven at 45° C. overnight to obtain the title compound as a white powder (117 g, 73%). LC-ES/MS m/z 468.0 (M+H).

Example 19

N-[(1 S)-2-[4-[2-[4-Amino-6-methyl-2-(trifluoromethyl)pyrimidin-5-yl]ethyl]-1-piperidyl]-1-methyl-2-oxo-ethyl]acetamide

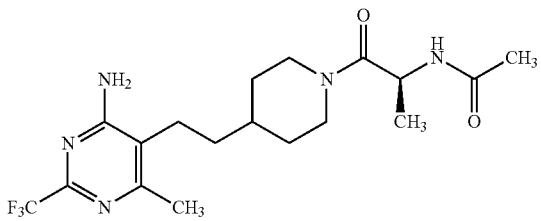 [SMILES: CC(=O)N[C@@H](C)C(=O)N1CCC(CCc2c(C)nc(C(F)(F)F)nc2N)CC1]

Prepare the title compound (47.7 mg, 67%) by essentially following the procedure described in Example 1, using (2S)-2-amino-1-[4-[2-[4-amino-6-chloro-2-(trifluoromethyl)pyrimidin-5-yl]ethyl]-1-piperidyl]propan-1-one (70 mg, 0.19 mmol), acetic anhydride (184.1 µL, 1.95 mmol) and DMAP (1.2 mg, 0.01 mmol) in DCM (3.9 mL, 0.05 M). ES/LC-MS m/z 402.2 (M+1).

Example 20

Methyl-[(1S)-2-[4-[2-[4-amino-6-methyl-2-(trifluoromethyl)pyrimidin-5-yl]ethyl]-1-piperidyl]-1-methyl-2-oxo-ethyl]carbamate

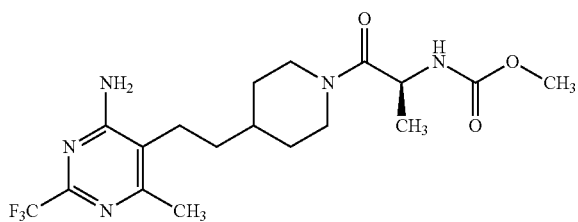 [SMILES: COC(=O)N[C@@H](C)C(=O)N1CCC(CCc2c(C)nc(C(F)(F)F)nc2N)CC1]

Dissolve (2S)-2-amino-1-[4-[2-[4-amino-6-methyl-2-(trifluoromethyl)pyrimidin-5-yl]ethyl]-1-piperidyl]propan-1-one (43.8 mg, 0.12 mmol) in DCM (3 mL) and add dimethyl dicarbonate (22.0 μL, 182.8 umol) and pyridine (30 μL, 365.6 μmol). Stir resulting mixture at RT overnight, pour into saturated aqueous NaCl (100 mL) and extract with DCM (3×30 mL). Wash combined organic layers with 0.1 N HCl (2×100 mL), water (100 mL), saturated aqueous NaCl (100 ml), dry over MgSO4, filter and concentrate under reduced pressure to obtain the title compound as an off-white solid (22 mg, 43%). LC-ES/MS m/z 418.2 (M+H).

Example 21

N-[(1S)-2-[4-[2-[4-Amino-6-methyl-2-(trifluoromethyl)pyrimidin-5-yl]ethyl]-1-piperidyl]-1-methyl-2-oxo-ethyl]pyridine-2-carboxamide hydrochloride

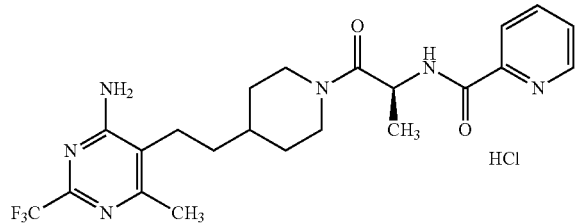 [SMILES: Cc1nc(C(F)(F)F)nc(N)c1CCC1CCN(C(=O)[C@H](C)NC(=O)c2ccccn2)CC1 ; Cl]

Dissolve N-[(1S)-2-[4-[2-[4-amino-6-methyl-2-(trifluoromethyl)pyrimidin-5-yl]ethyl]-1-piperidyl]-1-methyl-2-oxo-ethyl]pyridine-2-carboxamide (69 mg, 0.15 mmol) in DCM (1 mL) and add HCl (1M in dioxane, 500 mL). Stir at room temperature for 10 min, then concentrate under vacuum. Triturate resulting residue with DCM (1 mL) followed by Et$_2$O (2 mL). Filter and collect resulting light yellow solid to obtain the title compound (74 mg, 98%). LC-ES/MS m/z 465.2 (M+H).

Assays

GOAT is the principal enzyme that converts UAG to AG. For reviews of the role of GOAT and ghrelin see: Kristy M. Heppner et al, *The ghrelin O-acyltransferase-ghrelin system: a novel regulator of glucose metabolism*, Current Opinion in Endocrinology, Diabetes & Obesity 2011, 18:50-55; Phillip A. Cole et al., *Glucose and Weight Control in Mice with a Designed Ghrelin OAcyltransferase Inhibitor*, Science. 2010 Dec. 17; 330(6011): 1.689-1692. doi: 10.1126/science. 1196154, Matthias H. Tschöp et al., *Gastric O-acyl transferase activates hunger signal to the brain*, Proc Natl Acad Sci USA. 2008 Apr. 29; 105(17): 6213-6214, and Jesus Gutierrez, et al., *Ghrelin octanoylation mediated by an orphan lipid transferase*, Proc Natl Acad Sci USA., 2008 Apr. 29, 105 (17): 6320-6325.

The role of GOAT is supported by the phenotypes observed in mice devoid of GOAT gene. Therefore, inhibition of GOAT is expected to decrease circulating AG and raise circulating UAG. Consequently, the ratio of AG to total ghrelin (UAG+AG) is reduced after GOAT inhibitor treatment.

In Vitro Cell Free Human GOAT Enzymatic Assay

Human GOAT gene (Accession number: NM 001100916) is subcloned to pAN51 baculoviral expression vector. Baculovirus stock is prepared following the Bac-to-Bac Protocol provided by the vendor, Invitrogen, California, USA. Five mililiters of human GOAT baculoviral stock are added to 500 mL SDf cells in HyQ SFX-Insect™ media (HyClone catalog number SF130278.02) at the density of 1×10$^6$ cells per mililiter in a 2 L Erlenmeyer flask. The flask with human GOAT gene infected Sf9 cells is put on a plate shaker at 120 rpm at 28° C. for 48 hours. After 48 hours incubation, cells are centrifuged at 1,000×g for 10 min at 4° C. The cell pellets are collected and stored at −80° C. in a freezer until ready for further processing.

Preparation of Microsomal Membrane of GOAT Enzyme for the Enzymatic Assay:

One gram cell pellets are suspended in 9 mL chilled homogenization buffer (50 mM Tris-HCl, 250 mM sucrose, adjusted to pH 7.5 and sterile filtered through 0.2 μm Millipore filter). The cell suspension is transferred to a Dounce glass homogenizer. Cell pellets are homogenized with 40 strokes on ice. The homogenate is centrifuged at 3,000 rpm in a Beckman swing bucket rotor at 4° C. for 10 min to remove unbroken cells. The supernatant is collected and centrifuged at 40,000×g for 1 hour at 4° C. The resulting membrane pellet is suspended in the homogenization buffer using a Dounce glass homogenizer and stored at −20° C. in the freezer for the assay. For long term storage of the human GOAT enzyme membrane preparation, the suspended membrane is stored in a −80° C. freezer.

Human GOAT Enzymatic Assay Protocol:

Prepare test compounds in DMSO to make up a 0.2 mM stock solution. Serially dilute the stock solution in DMSO to obtain a ten-point dilution curve with final compound concentrations ranging from 10 μM to 0.5 nM in a 96-well round-bottom plate. Prepare enzyme and substrate solutions in assay buffer (0.02% TWEEN™-20 in 50 mM Tris, pH 7.5/250 mM sucrose/1 mg/mL BSA/10 mM EDTA). Add diluted compound (1 μL) to each well of row A to N of a corresponding low protein binding 384 well plate. Add human GOAT substrate mix (10 μL), consisting of human desacyl-ghrelin-biotin (CPC Scientific Inc., 6.0 μM final), octanoyl-coenzyme A (CoA) (Sigma, 60 μM final) and an AG specific antibody (WO 2006/091381)(1.0 fig/mL final), to the compounds. Add GOAT-His/sf9 enzyme preparation, that has been prepared in assay buffer (9 μL), to each well of the plate containing substrate and test compounds resulting in a final concentration of 0.01 μg/mL to initiate the reaction. Incubate the mixture for 1 hour at RT on a gently rotating oscillator. Add 4M guanidine hydrochloride (20 μL) to all wells, mix, and incubate for 3 hours to stop the reaction.

Prepare ELISA plates (STREPTAVIDIN SPECTRA-PLATE™ 384, Perkin Elmer) by blocking with 2% Heat-Inactivated FBS in PBS (40 µL) (Invitrogen) blocking buffer for 3 hours. Aspirate the blocking buffer from ELISA plate and add blocking buffer (23 µL) to columns 1-24, rows A-N. Reserve rows O and P for the acylghrelin standard curve. Add the reaction mix (2 µL) to the ELISA plates. Prepare a 10 point standard curve (biotin-labeled octanoyl-ghrelin) by serial 2× dilution in blocking buffer containing 0.2M Guanidine hydrochloride starting at 2.5 pM. Incubate the reaction mixture or biotin-labeled AG standard in the ELISA plate overnight at 4° C. The following day, wash the plate 3× with wash buffer (0.1% TWEEN™-20/PBS, 100 µL per well in each wash cycle). Add AG specific antibody (WO 2006/091381) (25 µL of 0.5 µg/mL in blocking buffer) to each well and incubate at RT for 1 hour. Wash the plate 3× with the wash buffer, similarly to the previous step. Add Protein G-HRP (25 µL)(Southern Biotech) diluted 3,000× in blocking buffer and incubate 1 hour at RT. Wash the late 3× with wash buffer, as in the previous steps. Add TMB reagent (25 µL) (Kirkegaard & Perry Laboratories, Inc.) to each well and let develop for 20 min and stop with 1M phosphoric acid (25 µL per well). Read plates at 450 nm using an ENVISION® Multilabel plate reader. AG levels are calculated versus a fitted standard curve and percent inhibition calculated. The 10-point inhibition curve is plotted and fitted with the four-parameter logistic equation to obtain $IC_{50}$ values using ACTIVITYBASE® (ver. 7.3.2.1).

Following a protocol essentially as described above, all of the compounds of the Examples herein were tested and exhibited an $IC_{50}$ for the in vitro cell free human GOAT enzymatic assay of lower than 1 µM. The following exemplified compounds of the invention were tested essentially as described above and exhibited the following activity as illustrated in Table 2 below.

TABLE 2

| Ex No. | $IC_{50}$ (nM) |
|---|---|
| 2 | 69.5 ± 0.6 (n = 2) |
| 15 | 55.7 (n = 1) |
| 17 | 420 (n = 1) |
| 18 | 276 (n = 1) |
| 20 | 615 (n = 1) |

The data in Table 2 demonstrate that the compounds of Table 2 inhibit purified GOAT enzyme activity in vitro.

Comparing the change in the ratio of AG to total ghrelin in the compound treated group and that of the vehicle treated group reflects the degree of GOAT enzyme inhibition in vivo, due to the dynamic processing of UAG to AG by the GOAT enzyme. In the in vivo pharmacodynamic studies herein, the levels of AG and UAG in plasma and stomach in the vehicle and compound treated groups are measured by ELISA specifically to these two analytes. The total ghrelin level of each sample is computed as the sum of AG and UAG by these ELISA measurements. The ratio of AG to total ghrelin is defined by the level of AG in each sample divided by the level of total ghrelin in the same sample. The levels of AG, UAG and ratio of AG to total ghrelin in the vehicle treated group is computed and set as 100%. The relative change of these parameters in the compound treated group is then computed to determine the effectiveness of the test compound.

In Vivo Dose Dependent 3 Day BID Study for GOAT Inhibitor:E

Animals and Treatment:

Purchase male C57BL/6 mice from Harlaan (Indianapolis, Ind.) at 9 weeks of age. House the mice individually in a temperature-controlled (24° C.) facility with a 12 hours light/dark cycle (lights on 2200 h), and allow free access to a standard rodent chow (diet 2014, Harlan) and water. Typically, use the mice when they are 10-13 weeks of age at the time of the study. On day 0 of the experiment, randomize the mice into treatment groups (N=7/group) so each group has similar mean body weights. On day 1 and day 2, treat the animals with vehicle (1% hydroxyethylcellulose, 0.25% TWEEN™ 80, 0.05% antifoam) or test compound prepared in the vehicle as suspension at various dosages by oral gavage at 7 am and 7 pm. On day 3, fast the animals, move them into clean cages and dose with vehicle or the test compound again at 8 am by oral gavage. That same day at 1 pm, sacrifice the animals by decapitation to collect blood. For details of blood collection and plasma treatments see Blood collection and Extraction of Ghrelin from Plasma section below.

Blood Collection:

Collect approximately 600 µL blood into a pre-weighed EDTA tube containing 600 µL (defined as $V_{preservative}$) freshly-prepared preservative (4 mM PEFABLOC® [4-(2-aminoethyl) benzenesulfonyl fluoride hydrochloride], 72 mM NaCl, 58 mM NaF, 0.032 N hydrochloric acid, pH 3.0) and mix immediately. Weigh the tube again and keep on ice. To accurately determine the exact blood volume of each sample using this blood collection procedure, the weight of the blood for each mouse is computed using the following equation:

Weight of Blood=(Weight of the tube containing Blood+preservative)−(Weight of the tube containing preservative)

Blood volume ($V_{blood}$)=(Weight of blood)/1.06

Note, the density of rodent blood is assumed as 1.06 g/mL.

Within 15 minutes after the blood collection, samples are centrifuged at 5000 rpm at 4° C. for 8 min. Remove plasma (650 µL) to a 5 mL glass tube containing 1 N hydrochloric acid (65 µL), mix and keep on ice.

Ghrelin Extraction by SEP-PAK® Column:

AG and UAG are extracted from plasma using SEP-PAK®_$C_{18}$ column to remove interference prior to performing the ELISA. The solid phase extraction of AG and UAG peptides by SEP-PAK®_$C_{18}$ columns can be performed on a vacuum manifold (Waters Corp) or using a peristaltic pump. The sample SEP-PAK®_column extraction procedure is independently applied to the plasma sample obtained from each individual mouse. The general extraction protocol is described as follows.

All solutions used for the entire protocol of the SEP-PAK® column extraction should be at ice cold condition. Wet SEP-PAK®_columns (WAT054960, Waters Corp, Milford Mass.) with 99.9% ACN/0.1% TFA (1 mL of solution of 100 mL ACN/0.1 mL TFA). Apply pressure to adjust the flow-rate to about 1 mL/min to remove liquid from the column bed but do not allow the column to dry out at any point. Once liquid is removed from the column, stop the pressure. Equilibrate the columns with 3% ACN/0.1% TFA (1 mL of 97 mL water, 3 mL ACN, 0.1 mL TFA). Apply pressure to adjust the flow-rate to about 1 mL/min to remove liquid from the column bed, but do not let the column dry out. Dilute approximately 650 µL acidified plasma (defined as $V_{plasma\ added\ to\ column}$) to 1.4 mL ice cold 0.1% TFA. Load all diluted acidified plasma from the previous step onto the columns. Apply pressure to adjust the flow-rate to about 0.5 mL/min to allow sample passing through the column and ghrelin peptides to absorb onto the resin of the column. Do not let the column dry out. Wash with 3% ACN/0.1% TFA (0.9 mL of 97 mL water, 3 mL ACN, 0.1 mL TFA). Apply pressure to adjust the flow-rate to about 1 mL/min to remove liquid from the column bed but do not let the column dry out. Repeat the wash two more times. Elute with 60% ACN/0.1% TFA (1 mL of 40 mL water, 60 mL ACN, 0.1 mL TFA). Put a collection tube underneath of each column, apply pressure to adjust the flow-rate to about 0.5 mL/min to push liquid through the column and collect the eluent into the collection tube. Freeze the samples on dry ice immediately. Lyophilize the samples in a speed-vac (Model# SC110A, Savant) and store at −20° C. until the ELISA assay is performed.

ELISA Assay for Ghrelin:

Coat 96-well MULTI-ARRAY® MSD® plates (Meso Scale Discovery, Gaithersberg, Md., Catalog # L15XA-3) with 100 µL of 1 µg/mL of an antibody (WO 2005/026211 AND WO2006/019577) that recognizes the mid-domain of both the acyl and unacylated forms of ghrelin in PBS (Invitrogen). Tap the sides of the plates to ensure coverage of wells, seal with adhesive plate sealer, and incubate overnight at RT. Discard the contents and add BLOCKER™ Casein in PBS (25 µL) (Thermo Scientific, Rockford, Ill., Catalog #37528) to each well. Reseal the plates and put on a plate shaker at RT for 1 hour.

Reconstitute the lyophilized preserved plasma samples from the SEP-PAK® $C_{18}$ column extraction in BLOCKER™ Casein in PBS (400 µL to each sample, this volume is defined as $V_{reconstitution}$), mix well with a vortex mixer and incubate on ice for 45-60 min. Discard the contents from the plates and add reconstituted plasma samples at 25 µL to each well. Prepare acylghrelin and unacylated ghrelin standard curves beginning with 8000 pg/mL and performing serial 1:4 dilutions for 8 total concentrations. Add the prepared standards in duplicate to the blocked plates with 25 µL in each well. Seal the plates and incubate at RT on a plate shaker for 2 h.

Discard the plate contents and wash three times with PBS including 0.1% TWEEN™ 20 (150 µL)(PBS-T). Acylghrelin specific antibody (WO 2006/091381) or unacylated ghrelin specific antibody (WO 2006/055347) labeled with MSD® SULFO-TAG™ (Meso Scale Discovery) are diluted to 0.05 µg/mL in 0.2× Blocker Casein containing 0.05% TWEEN™ 20, named secondary antibody solution. Remove the final wash and add secondary antibody solution (25 µL to each well) which specifically recognizes AG or UAG. The plates are resealed and incubated for 1 hour at RT on a plate shaker before finally washing 3× again with PBS-T (150 µL/well).

Discard the final wash and replace with 1×MSD® Read Buffer (150 µL/well). Read the electrochemiluminescent signal generated by activation of the bound MSD® SULFO-TAG™ label to the electrodes on the plates using the MSD® SECTOR® Imager 6000 analyzer (Meso Scale Discovery). Calculate concentrations of acylghrelin or unacylated ghrelin based on the respective standard curve generated by the MSD® software. Determine the actual plasma concentration for each sample by multiplying the measured acylghrelin or unacylated ghrelin level by a dilution factor. The dilution factor for each plasma sample is computed with the following equation.

$$\text{Dilution Factor} = \left(\frac{V_{blood} + V_{preservative}}{V_{blood}}\right) \times \left(\frac{V_{reconstitution}}{V_{plasma\ loaded\ to\ column}}\right)$$

Results:

Administration of the compound of Example 2 for 3 days decreases plasma AG by 40%, 60%, 56%, 63%, and 63%, and increases UAG by 2.10, 2.22, 3.57, 3.49 and 3.78 fold, respectively at 0.1, 0.3, 1, 3, and 10 mg/kg (results tabulated below). Administration at 0.1, 0.3, 1, 3, and 10 mg/kg results in 57, 62, 79, 82 and 82% reduction respectively in AG to total ghrelin ratio when compared to the vehicle-treated control animals.

TABLE 3

| Treatment | AG (% of control) | UAG (% of vehicle control) | AG/Total-ghrelin (% of vehicle control) |
|---|---|---|---|
| Vehicle | 100 (n = 7) | 100 (n = 7) | 100 (n = 7) |
| 0.1 mg/kg | 60 ± 8 (n = 7) | 210 ± 43 (n = 7) | 43 ± 3 (n = 7) |
| 0.3 mg/kg | 40 ± 10 (n = 7) | 222 ± 54 (n = 7) | 28 ± 1 (n = 7) |
| 1 mg/kg | 44 ± 6 (n = 14) | 357 ± 30 (n = 14) | 21 ± 1 (n = 14) |
| 3 mg/kg | 37 ± 9.6 (n = 14) | 349 ± 41 (n = 14) | 18 ± 5 (n = 14) |
| 10 mg/kg | 37 ± 9.9 (n = 7) | 378 ± 59 (n = 7) | 18 ± 3 (n = 7) |

The results demonstrate that the compound of Example 2 suppresses AG production and elevates the UAG in circulation, as shown in the GOAT knock-out mouse, in vivo.

We claim:

1. A compound of formula

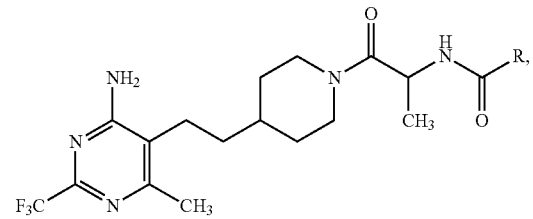

wherein R is selected from —$C_1$-$C_3$ alkyl optionally substituted with —OH; —$OC_1$-$C_4$ alkyl; pyrazolyl, oxazolyl, thiazolyl, or thiadiazolyl, wherein pyrazolyl, oxazolyl, or thiazolyl each may be optionally substituted one to two times with —$CH_3$; pyridinyl, pyridazinyl, or pyrazinyl, wherein each may be optionally substituted with —Cl; and phenyl optionally substituted with —$OCH_3$; or a pharmaceutically acceptable salt thereof.

2. The compound of claim 1 wherein R is selected from —$CH_3$ optionally substituted with —OH; —$OCH_3$ or —$OC(CH_3)_3$; pyrazolyl, oxazolyl, thiazolyl, or thiadiazolyl, wherein pyrazolyl, oxazolyl, or thiazolyl each may be optionally substituted one to two times with —$CH_3$; pyridinyl, pyridazinyl, or pyrazinyl, wherein each may be optionally substituted with —Cl; and phenyl optionally substituted with —$OCH_3$; or a pharmaceutically acceptable salt thereof.

3. The compound of claim 1 wherein R is selected from pyrazolyl, oxazolyl, thiazolyl, or thiadiazolyl, wherein pyrazolyl, oxazolyl, or thiazolyl each may be optionally substituted one to two times with —$CH_3$; pyridinyl or pyrazinyl, wherein each may be optionally substituted with —Cl; and phenyl optionally substituted with —$OCH_3$; or a pharmaceutically acceptable salt thereof.

4. The compound of claim 1 wherein the configuration of the carbon atom with the methyl substituent is (S):

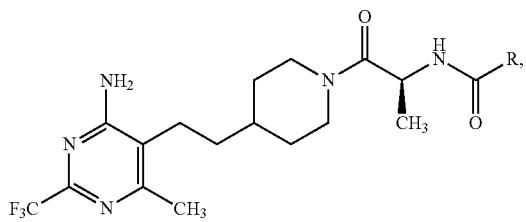

or a pharmaceutically acceptable salt thereof.

5. The compound of claim 1 of the formula

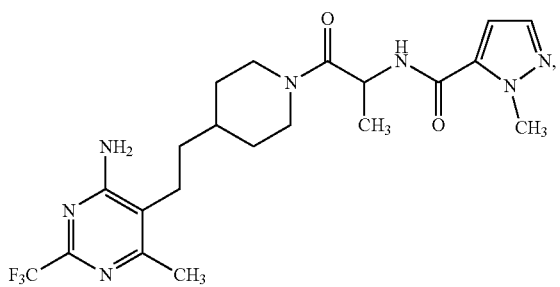 [SMILES: Cc1nc(C(F)(F)F)nc(N)c1CCC1CCN(C(=O)C(C)NC(=O)c2ccnn2C)CC1]

or a pharmaceutically acceptable salt thereof.

6. The compound of claim 5 of the formula

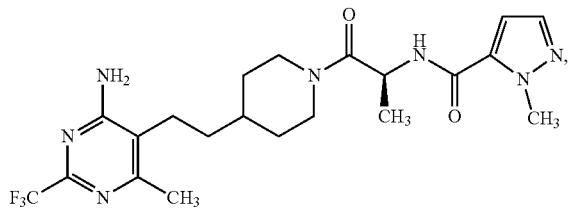 [SMILES: Cc1nc(C(F)(F)F)nc(N)c1CCC1CCN(C(=O)[C@H](C)NC(=O)c2ccnn2C)CC1]

or a pharmaceutically acceptable salt thereof.

7. The compound of claim 6 of the formula

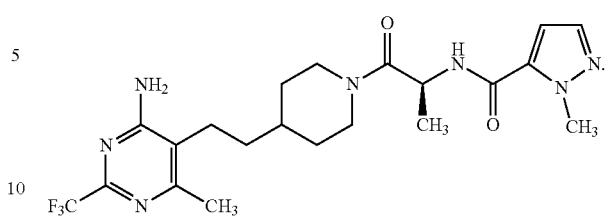

8. A pharmaceutical composition comprising a compound of claim 1, or a pharmaceutically acceptable salt thereof, with one or more pharmaceutically acceptable carriers, diluents, or excipients.

9. The pharmaceutical composition according to claim 8 in combination with one or more other therapeutic agents.

10. A method of reducing weight gain comprising administering a compound according to claim 1, or a pharmaceutically acceptable salt thereof, to a patient in need thereof.

11. A method of reducing weight regain comprising administering a compound according to claim 1, or a pharmaceutically acceptable salt thereof, to a patient in need thereof.

12. A method of treating obesity comprising administering a compound according to claim 1, or a pharmaceutically acceptable salt thereof, to a patient in need thereof.

13. A method of treating type 2 diabetes comprising administering a compound according to claim 1, or a pharmaceutically acceptable salt thereof, to a patient in need thereof.

14. A method of reducing weight gain comprising administering a compound according to claim 6, or a pharmaceutically acceptable salt thereof, to a patient in need thereof.

15. A method of reducing weight regain comprising administering a compound according to claim 6, or a pharmaceutically acceptable salt thereof, to a patient in need thereof.

16. A method of treating obesity comprising administering a compound according to claim 6, or a pharmaceutically acceptable salt thereof, to a patient in need thereof.

17. A method of treating type 2 diabetes comprising administering a compound according to claim 6, or a pharmaceutically acceptable salt thereof, to a patient in need thereof.

* * * * *